United States Patent [19]
Lai

[11] Patent Number: 5,112,319
[45] Date of Patent: May 12, 1992

[54] INFUSION ALARM SYSTEM

[76] Inventor: Eric Lai, 3F, No. 1, La. 119, Baoyi Rd., Taipei, Taiwan

[21] Appl. No.: 699,717

[22] Filed: May 14, 1991

[51] Int. Cl.$^5$ .................. A61M 5/00; G08B 21/00
[52] U.S. Cl. .................. 604/246; 128/DIG. 13; 340/613; 116/109; 200/85 R; 177/45; 177/225
[58] Field of Search .................. 604/65, 122, 245, 246, 604/260; 128/DIG. 13; 340/613, 618; 116/109; 200/85 R; 177/45, 48, 115, 116, 232, 225, 233

[56] References Cited

U.S. PATENT DOCUMENTS

| | | | |
|---|---|---|---|
| 2,706,755 | 4/1955 | Krasno | 128/DIG. 13 |
| 3,105,490 | 10/1963 | Schoenfeld | 177/245 |
| 3,107,745 | 10/1963 | Bujan | 177/232 |
| 3,287,721 | 11/1966 | Baehr | 128/DIG. 13 |
| 3,389,387 | 6/1968 | Hulse et al. | 128/DIG. 13 |
| 3,390,238 | 6/1968 | O'Neil | 128/DIG. 13 |
| 3,425,415 | 2/1969 | Gordon | 340/613 |
| 3,656,138 | 4/1972 | Hamma | 128/DIG. 13 |
| 4,137,915 | 2/1979 | Kamen | 128/DIG. 13 |
| 4,176,349 | 11/1979 | Fligel | 340/613 |
| 4,198,626 | 4/1980 | Rauscher | 604/246 |

Primary Examiner—John D. Yasko
Assistant Examiner—Anthony Gutowski
Attorney, Agent, or Firm—Bacon & Thomas

[57] ABSTRACT

An infusion alarm system comprised of a housing, an upper cover attached to the housing at the top, a control circuit set in said upper cover, a battery box set inside the housing and an inner shell set between the housing and the battery box, a tension spring set in the inner shell having a hook coupled thereto at the bottom for suspending a drip infusion bottle, an adjusting key set set in the housing to adjust the tension of the tension spring. When the weight of the drip infusion bottle is reduced to a predetermined range due to reducing of infusion solution during drip infusion operation, the control circuit is triggered to produce audio and visual alarm signals through an audio and a visual alarm device respectively.

3 Claims, 6 Drawing Sheets

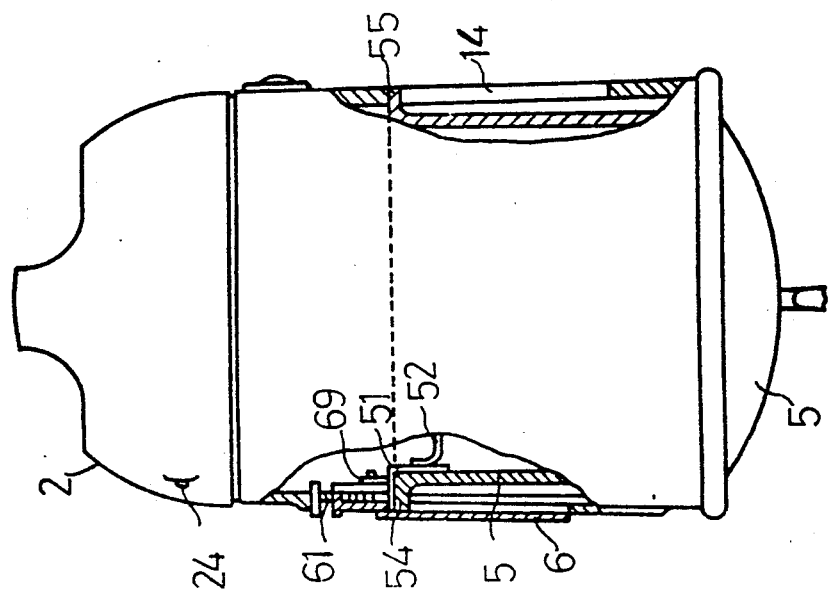
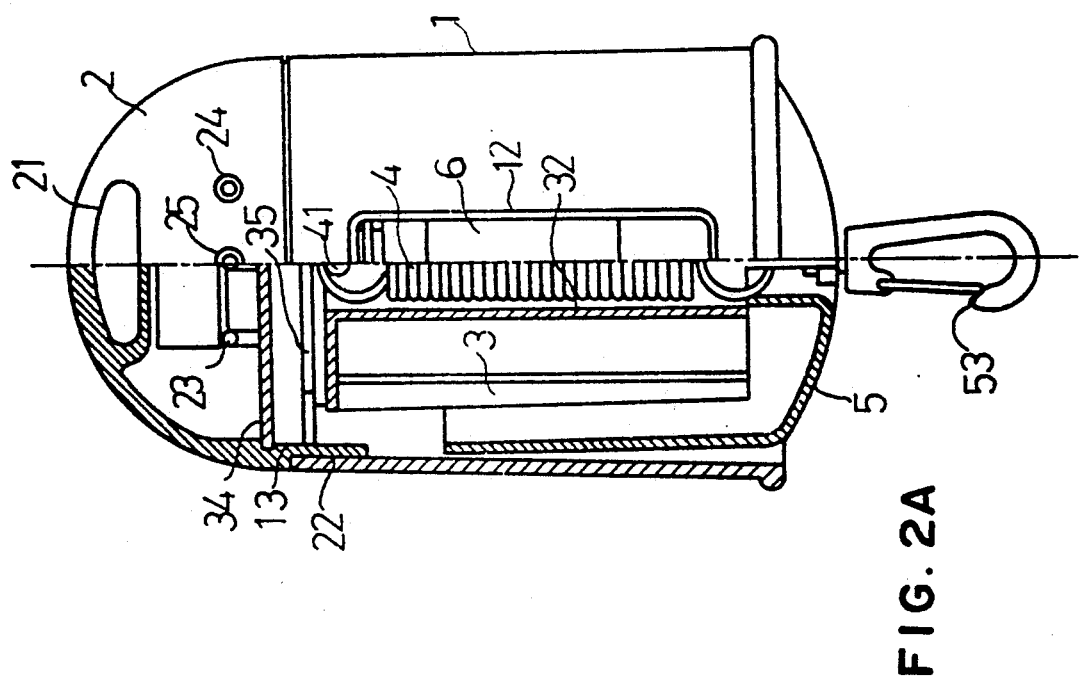

INFUSION ALARM SYSTEM

BACKGROUND OF THE INVENTION

The present invention relates to a kind of infusion alarm system and relates more particularly to such an infusion alarm system which can be adjusted to produce audio as well as visual alarm when the infusion solution in a drip infusion bottle is reduced below a predetermined level.

During drip infusion operation, the infusion solution in a drip infusion bottle will be completely transfused into the body of a patient several hours after injection of the needle. During drip infusion process, the nurse on duty or the family of the patient in treatment must be frequently observing the glass adapter of the drip infusion set so as to stop infusion by the regulating clamp and prevent outside air from entering the patent's vessel.

Further, commercialized drip infusion bottles are generally made in volume of 500 cc or 1000 cc. In case a patient does not require such a big volume, prescribed infusion volume is generally measured through the eyes during drip infusion operation. However, it is difficult to accurately control the volume in infusion through visual check. Further, a nurse must be very carefully watching the drip infusion bottle during drip infusion operation.

SUMMARY OF THE INVENTION

The present invention has been accomplished to eliminate the aforesaid problems. It is therefore an object of the present invention to provide an infusion alarm system which has three light emitting diodes including a green LED to indicate operating mode, a yellow LED to indicate power low voltage, and a red LED to indicate completion of infusion. It is still another object of the present invention to provide an infusion alarm system which is compact and easy to operate.

To achieve the above objects, there is provided an infusion alarm system which is generally comprised of a housing having a tension spring fastened therein to hold a hook for suspending a drip infusion bottle. When the weight of the drip infusion bottle is reduced to a predetermined range due to reducing of infusion solution during drip infusion operation, two contacts are connected forming into a short circuit causing an audio and a visual alarm device to produce audio and visual alarm signals. Because the infusion alarm system is triggered to produce audio and visual alarm signals due to great change of loading weight, the present invention can be used for any drip infusion bottles either made of glass or plastic material.

BRIEF DESCRIPTION OF THE DRAWINGS

FIGS. 2A and 2B are sectional assembly views of the preferred embodiment of the infusion alarm system of the present invention respectively taken in two different directions;

DETAILED DESCRIPTION OF THE PREFERRED EMBODIMENT

Figure 1:
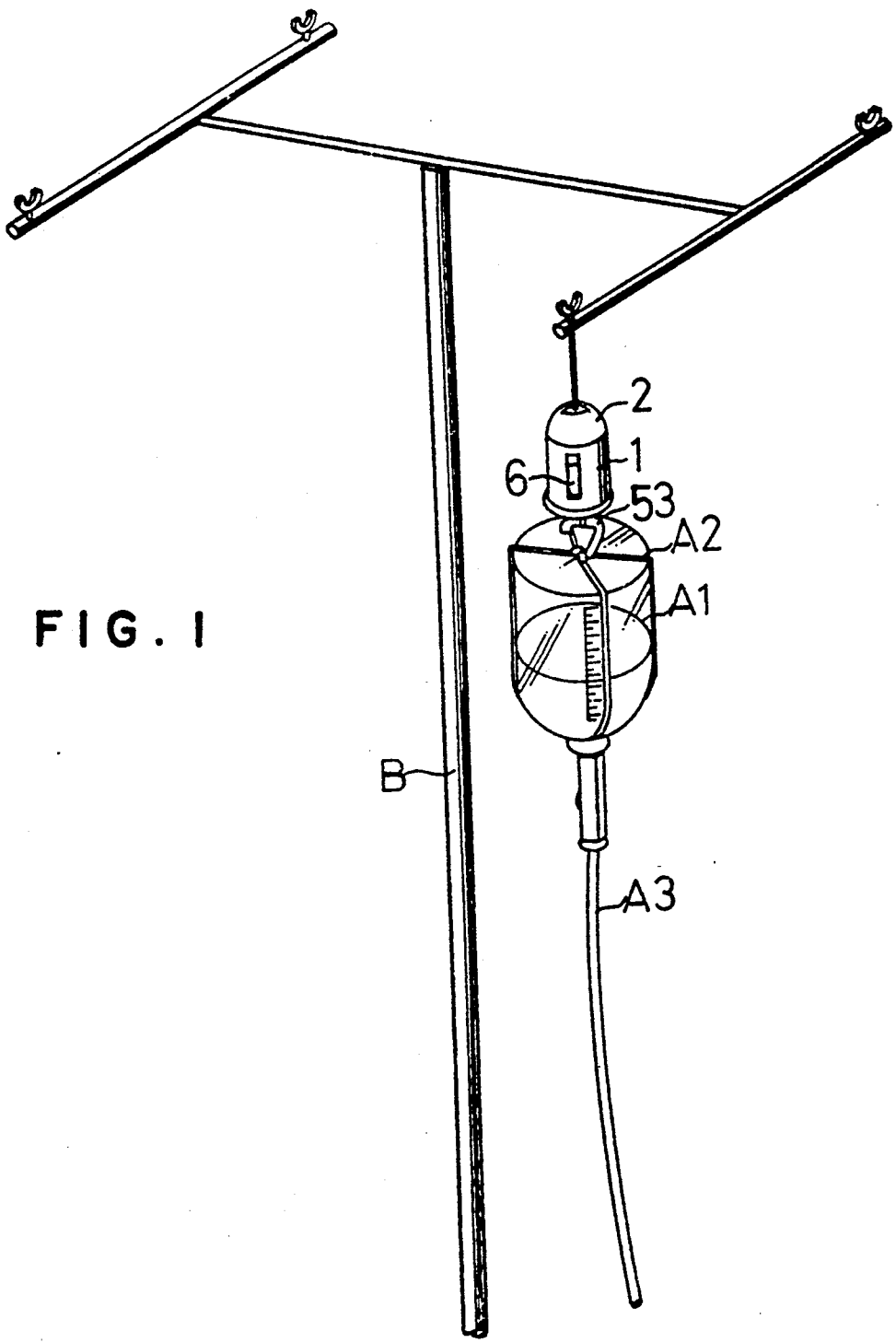
FIG. 1 illustrates an infusion alarm system of the present invention suspended from a drip infusion stand to hold a drip infusion bottle.

Referring to FIG. 1, an infusion alarm system accordance with the present invention is generally comprised of a housing 1 having an upper cap 2 suspended from a drip infusion stand B by a rope and a hook 53 at the bottom to hook up the binding wire A2 of a drip infusion bottle A1 permitting the plastic tubing A3 of said drip infusion bottle A1 to be smoothly extending downward, wherein the housing 1 has an adjusting key set 6 through which infusion dosage is controlled.

Figure 3:
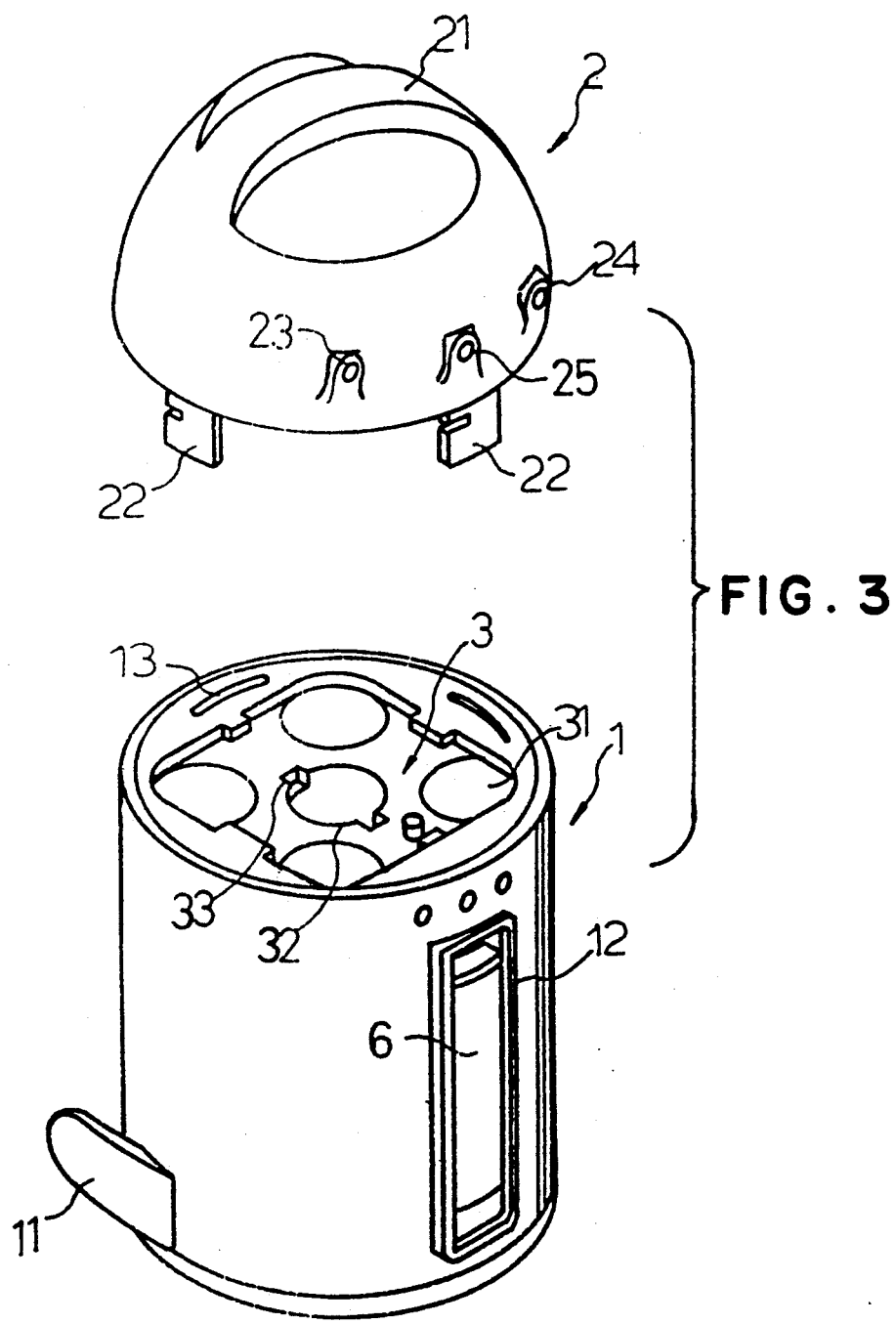
FIG. 3 is a perspective view of the preferred embodiment of the present invention wherein the upper cover is removed from place.
Figure 5:
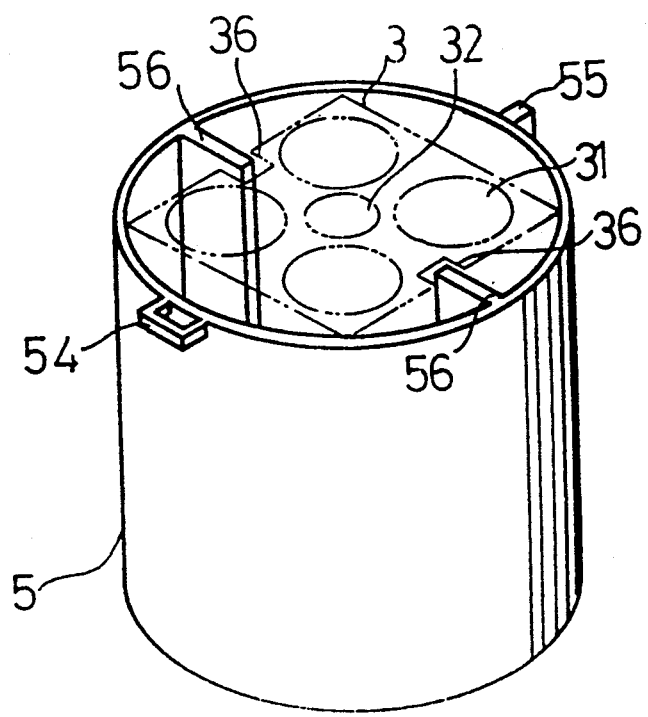
FIG. 5 illustrates the positioning of the battery box in the inner shell.
Figure 5A:
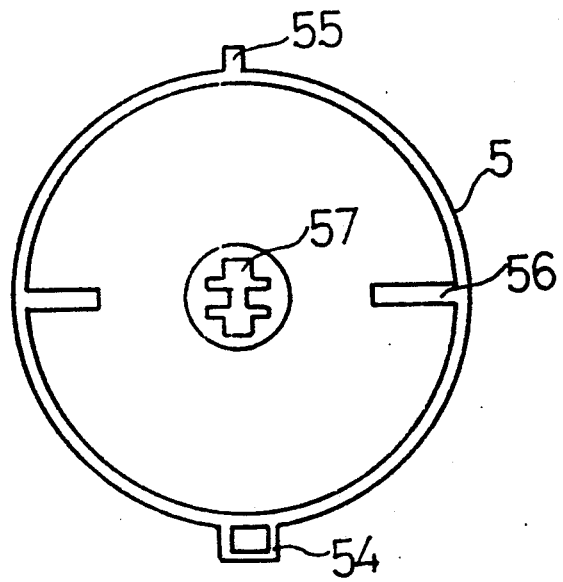
FIG. 5A is a top view of the inner shell.
Figure 6A:
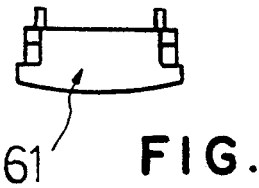
FIGS. 6A, 6B, 6C, and 6D illustrate several side views of the adjusting key set taken in different directions.
Figure 6B:
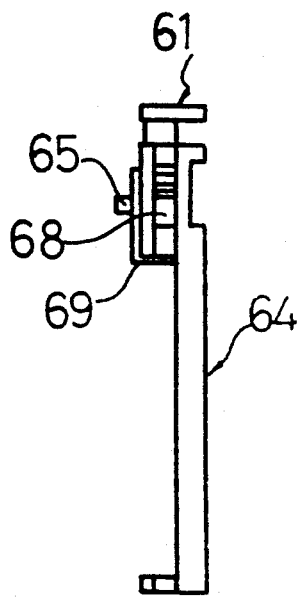
Figure 6C:
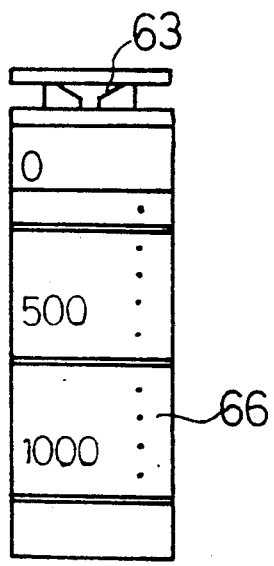
Figure 6D:
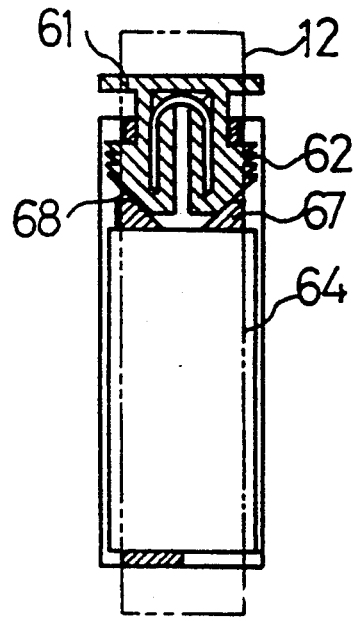

Referring to FIGS. 2A, 2B, and 3, housing 1 is made in cylindrical shape having two legs 11 bilaterally externally disposed at a lower end, four retaining slots 13 spaced from one another at equal interval and disposed at an upper end around the inner wall thereof, a toothed, rectangular window 12 at the front face thereof, a guide groove 14 vertically disposed at the back side thereof. Upper cover 2 is attached to the housing 1 at the top, having a hanger portion 21 at the top, four hooked strips 22 peripherally disposed at the bottom at equal interval, and three light emitting diodes namely green LED 23, Yellow LED 24 and Red LED 25 respectively made on the front face thereof. Inside the housing 1, there is provided a battery box 3 having four battery chambers 31 vertically disposed at the four corners thereof, a spring mounting hole 32 vertically disposed at the center and two guide grooves 36 vertically disposed at two opposite sides (see FIG. 5). A pin retaining hole 33 is transversely disposed at the top end of the spring mounting hole 32. A conductive battery cover 35 is attached to the battery box 3 covering over the battery chambers 31 and coupled to a circuit board 34 which is attached thereto at the top. Between the housing 1 and the battery box 3, there is provided an inner shell 5 made in a cup-like shape having a projecting strip 54 transversely projecting outwards at the top and incorporated with a copper strip 51 and connected to the circuit board 34 via a conductor 52, two elongated projecting plates 56 vertically disposed at two opposite locations on the inner wall surface thereof and respectively engaged in the two guide grooves 36 of the battery box 3, a projecting guide block 55 externally disposed opposite to said projecting strip 54 and engaged in the guide groove 14 of the housing 1 (see FIGS. 2B and 5), and a hook 53 at the bottom. There is also provided a tension spring 4 set in the spring mounting hole 32, one end secured to a locating pin 41 which is fastened in the pin retaining hole 33 at the top end of the spring mounting hole 32 and an opposite end coupled with the hook 53 of the inner shell 5. The inner shell 5 further has a retaining slot 57 in shape as shown in FIG. 5-A, which is provided for holding the hook 53 in position and presenting a drip infusion bottle from rotating.

Referring to FIG. 2B again and seeing FIGS. 6A–6D, adjusting key set 6 is generally comprised of an inner key 61 and an outer key 64 engaged in the toothed, rectangular window 12 of the housing 1. The inner key has a plurality of teeth 62 disposed at two opposite sides and respectively sloping in one direction and engaged with the teeth on the periphery of the toothed, rectangular window 12, an invertedly disposed triangular bottom end 63, and a strip spring 63 fastened in a slot made therein. The outer key 64 is made from an elongated, transparent board having graduation 66 made on the outer wall surface thereof, a top opening at the top through which the inner key 61 is inserted, two side openings at two opposite sides through which the teeth 62 of the inner key 61 are exposed to engage with the teeth of the toothed, rectangular window 12, two stop means at the inside to limit the down stroke of the inner key 61 in the outer key 64, a projecting rod 65 at the back coupled with a conductive strip 69 connected to the circuit board 34 via a conductor 52.

The projecting guide block 55 and the elongated guide plates 56 of the inner shell 5 are respectively engaged with the guide groove 14 of the housing 1 and the guide grooves 36 of the battery box 3 for smooth sliding and overload protection.

Figure 7A:
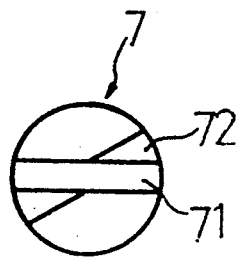
FIGS. 7A and 7B illustrate the structure of the one-way screw.
Figure 7B:
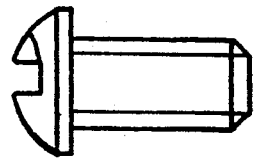

Referring to FIGS. 7A and 7B, a one-way screw 7 is used to fasten the upper cover 2 to the housing 1. The one-way screw 7 has a straight slot 71 on the top of the head thereof, two bevel, tangent planes 72 disposed at two opposite locations through said straight slot 71. Because the one-way screw 7 can only be screwed inwards to tightly fasten the upper cover 2 to the housing 1 and is prohibited from being driven to screw outwards, once the upper cover 2 is fixedly secured to the housing 1, the internal precision structure of the housing 1 is well protected.

The operation of the present invention is outlined hereinafter. After the infusion alarm system of the present invention is suspended from a drip infusion stand, suspend a drip infusion bottle A1 from the hook 53 permitting the inner shell 5 to be pulled downwards and the tension spring 4 to be simultaneously pulled to expand so as to equilibrate the load (if loaded weight surpasses the tensile force of the tension spring, the guide block will be stopped at the bottom end of the guide groove 14) and, the projecting strip 54 of the inner shell 5 is disposed at a position on the transparent outer key 64 to indicate the relative weight of the drip infusion bottle through the graduation 66. Presume the volume in the suspended drip infusion bottle A1 is 500 cc and prescribed infusion dosage is 300 cc, thus, press the inner key 61 to release the tooth 62 from the tooth of the rectangular window 12 and then, move the adjusting key set 6 downwards to the location where the graduation indicates 300 cc and lock in in position.

During drip infusion operation, the tension spring 4 is gradually returning to its original shape while the infusion solution in the drip infusion bottle A1 is gradually reducing and, at the same time, the inner shell 5 is simultaneously moving upwards. As soon as the inner shell 5 is moved upwards to such an extent that the copper strip 51 of the projecting strip 54 contacts the conductive strip 69 of the adjusting key set 6 to produce short circuit, buzzer and LED are simultaneously triggered to give audio and visual warning signal.

Figure 4:
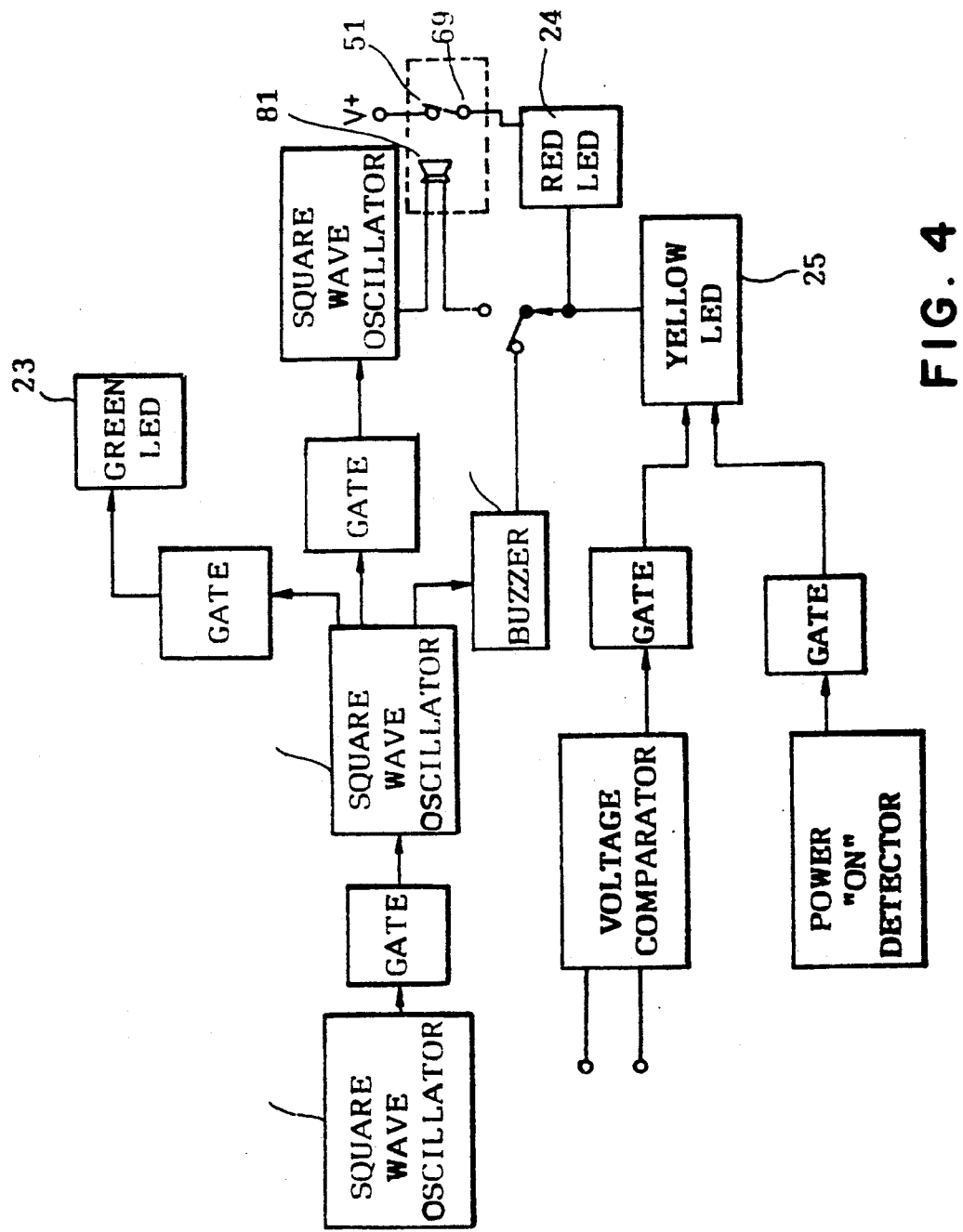
FIG. 4 is a control circuit block diagram according to the present invention.

The operation of the circuit of the present invention is outlined hereinafter with reference to FIG. 4:

When electric power supply is connected, the three light emitting diodes 23, 24 and 25 are simultaneously turned on and at the same time, the buzzer 8 is triggered to buzz, showing that the device is under normal condition and then, the green LED 23 flashes intermittently showing that the device is under operation;

When the Yellow LED 25 is turned on to flash continuously, it indicates that power failure or low voltage;

When the copper strip 51 and the conductive strip 69 are connected together causing short circuit, the red LED 24 flashes and the buzzer 8 buzzes continuously.

Further, an external earphone 81 may be used to replace the buzzer 8 for receiving audio alarm signal, which may be directly connected to the nurses' station for on-line operation.

The foregoing detailed description is given for clearness of understanding only and no unnecessary laminations should be understood therefrom, as modifications well be obvious to those skilled in the art.

What is claimed is:

1. An infusion alarm system, comprising:
   a housing in cylindrical shape having two legs bilaterally externally disposed at a lower end, a plurality of retaining slots spaced from one another at equal intervals and disposed at an upper end around the inner wall thereof, a toothed, rectangular window at the front face thereof, a guide groove vertically disposed at the back side thereof;
   an upper cover secured to said housing at the top by a screw means, having a hanger portion at the top for suspending from a drip infusion stand, a plurality of hooked strips around the periphery thereof and respectively hooked in said retaining slots of said housing, three LEDs on the front face thereof including a green, a yellow and a red;
   a battery box set inside said housing, having a center hole vertically disposed at the center with a tension spring set therein, a plurality of battery chambers vertically disposed around said center hole for holding dry batteries, a pin retaining hole transversely disposed at the top of said center hole with a pin fastened therein to suspend said tension spring, a conductive battery cover at the top covering over said battery chamber and said center hole, a control circuit fastened inside said conductive battery cover, and two guide grooves externally vertically disposed at two opposite sides;
   an inner shell movably set between said housing and said battery box, made in a cup-like shape, having a projecting strip transversely projecting outwards at the top and incorporated with a copper strip and connected to said circuit board by a conductor, two elongated projecting plates vertically disposed at two opposite locations on the inner wall surface thereof and respectively engaged in the two guide grooves of said battery box, a projecting guide block externally disposed at a location opposite to said projecting strip and engaged in the guide groove of said housing, and a hook suspended from said tension spring at the bottom for holding a drip infusion bottle;
   an adjusting key set comprised of an inner key and an outer key and movably engaged in said toothed, rectangular window of said housing, said inner key having a plurality of teeth at two opposite sides sloping in one direction and engaged with the teeth of said toothed, rectangular window, a finger-press portion at the top, an invertedly disposed triangular bottom end, a hollow space at the inside with a strip spring set therein, said strip spring being to extend outwards forcing the teeth of said inner key to engage with the teeth of said toothed, rectangular window, said outer key being made of an elongated, transparent board having graduation made on the outer wall surface thereof, a top opening at the top for inserting said inner key, two side openings at two opposite sides through which the teeth of said inner key are exposed to engage with the teeth of said toothed, rectangular window, two tapered stop blocks bilaterally disposed at the bottom inside said top opening to limit the down stroke of said inner key in said outer key, and a projecting rod at the back coupled with a conductive strip connected to said circuit board through a conductor;

wherein suspending said drip infusion bottle from said hook causes said tension spring to expand; reducing of infusion solution in said drip infusion bottle during drip infusion process causes said tension spring to pull up said inner shell permitting said copper strip of said inner shell to connect with said conductive strip of said adjusting key set so as to drive said control circuit to produce audio and visual alarm signals.

2. The infusion alarm system of claim 1, wherein said control circuit in said battery box is connected with a buzzer to give an audio alarm signal when said copper strip is connected with said conductive strip.

3. The infusion alarm system of claim 1, wherein said control circuit in said battery box has an earphone jack for sending an audio alarm signal through an external earphone, which may be directly connected to the nurses' station for on-line operation.

* * * * *